July 29, 1975
J. C. MIKKELSEN
Plant Pat. 3,753
BEGONIA PLANT
Filed July 10, 1974
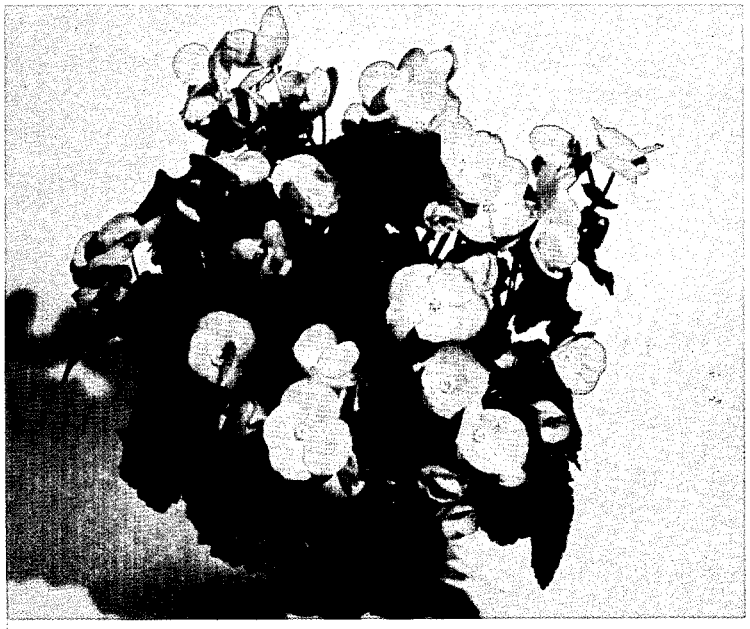

United States Patent

Plant Pat. 3,753

Patented July 29, 1975

3,753

BEGONIA PLANT

James C. Mikkelsen, Ashtabula, Ohio, assignor to Mikkelsens Inc., Ashtabula, Ohio Filed July 10, 1974, Ser. No. 487,397

Int. Cl. A01h *5/00*

U.S. Cl. Plt.—68 1 Claim

The present invention relates to a new and distinctive variety of begonia plant, botanically known as *Begonia elatior,* (B × *hiemalis*-Fotsch), discovered by me as a mutation on a flowering stock plant of the elatior begonia Krefeld Orange (U.S. Plant Pat. 3,403). The new cultivar appeared on a stem showing flowers having very dark red tepals. Asexual reproduction by stem and leaf cuttings has reproduced the unique features of the new variety through successive propagations.

The following characteristics distinguish the new begonia from parent:

1. Dark red tepals compared to Krefeld Orange; quite frequently the new variety flowers with six tepals.
2. Anthers are deeper yellow than the anthers of Krefeld Orange.

The following characteristics distinguish both the new variety and its parent Krefeld Orange from other begonias commercially known and used in the floriculture industry:

1. Plants are more vigorous but maintain the short compact growth habit of the cultivar Schwabenland, the parent of Krefeld Orange.
2. Internodal spacing is close.
3. Foliage is above average in size, heart shaped, indented, highly glossy, durable, and mildew resistant.
4. Leaves, leaf petiole, and main stems are highly colored with red pigmentation.
5. Older leaves develop a very dark appearance because of the additional pigmentation, thereby offering a new contrast to the flowers.
6. The new variety is very floriferous, capable of commercial utilization on a year around basis.
7. Vegetative reproduction is readily accomplished through propagation of leaf cuttings that root quickly and abundantly, eventually developing basal adventitious shoots allowing for the development of a full plant easily controlled for commercial forcing.

The accompanying colored photographic drawing illustrates the overall appearance of the new variety taken as a face view of the plant and showing the colors as true as it is reasonably possible to obtain in a colored reproduction of this type.

The following is a detailed description of my new begonia variety based on plants produced under commercial practices in Ashtabula, Ohio. Color references are made to the Royal Horticultural Society Colour Chart except where general color terms of ordinary dictionary significance are used.

Parentage: Mutation of Krefeld Orange.

Propagation: By asexually propagating many thousands of leaf cuttings, then growing those plants that formed adventitious bud shoots from the base of the leaf petiole and subsequently flowering those plants, it has been demonstrated repeatedly that the mutation is stable and produces true to type.

Rooting habit: Rapid and voluminous production of roots is above average for a begonia of this type. The initiation of adventitious buds on the base of the petiole that develop into vegetative shoots in a short period of time after root initiation is excellent.

Form: Plants tend to be compact with some self-branching giving a semi-dwarf appearance.

Habit of growth: The mutation is very vigorous with strong up right stems having close internodes. The increased vigor is very pronounced in comparison to an earlier mutation commercially known as Schwabenland Orange. This increased vigor allows for a better quality plant during the dull periods of winter.

Blooming habits: Flowers are usually single with four tepals, although six tepals frequently occur. Blooms flower one at a time carried on trusses. Blooms will usually endure for several weeks. The number of actual blooms vary with the age of the plant and the time of year. When the flowering response has been properly initiated, a general profusion of blooms occurs.

Blooming season: The natural flowering season of the new mutation is late November through early December. When proper regulation of the photoperiod is applied in conjunction with proper temperature manipulations, the new begonia variety can be brought into flower at any season of the year, making it of further economic value. The intense orange red color of the flowers is acceptable for all seasons. The color contrast of the foliage gives this variety another interesting and useful quality especially for the autumn, winter, and spring seasons.

Foliage: The foliage of the new variety has the same general features of the parent Krefeld Orange varitey. The foliage is alternate; borne at a sharp angle to the stem; average to above average in quantity with the following detailed descriptions:

*Size.*—Foliage would be classified as being rather large for this type of begonia. Environmental conditions can greatly alter the size, texture, and color tones of the foliage.

*Shape.*—The photographic drawing clearly shows the overall oval pointed type leaf with strong indentations similar to a maple leaf. A heart shape is apparent with the setback of the leaf petiole.

*Texture.*—The upper surface of the leaf is leathery in texture but has a luminescence or sparkle when the plant is grown with good cultural practices. The under surface of the leaf is glossy as if coated with a film of oil, giving a highly reflective appearance.

*Margin.*—The young foliage especially is quite indented and notched along the edges. As the foliage matures the edges become less indented; the overall leaf flattens and cups slightly downward in an umbrella effect.

*Color.*—New foliage: Upper side is green, heavily overlaid with deep red. Under side is dull red toward a shade of red 46–A to 59–B. Mature foliage: Upperside is green varying from 139–A to 135–A, with a light overlay of red giving a very dark leaf appearance. The underside of the leaves are yellowish green 147–B, with distinct red pigmentation.

Stems-petioles: The leaf petioles have a strong red coloring approaching a red purple 59–A. The stems when immature also have this type of coloration but become a brownish red to a dark green as they mature.

Disease resistance: The foliage is quite resistant to common mildew infections when compared with other begonia cultivars commonly used in the floricultural industry.

Flowers: Borne on pyramidal trusses with several clusters of three to a stem. Individual flower stems are short to medium in length with sufficient vigor to be upright and self-supporting. Tepals are relatively flat, usually four in number. The vigor of the plant is also expressed in the blooms which have a relatively strong texture and good overall quality. The flowers are nearly exclusively male with a distinctive yellow eye made up of a cluster of stamens and anthers. The flowers are one to two cm. smaller than Krefeld Orange, being four to five cm. in diameter.

Quantity: Very floriferous with flower development over a considerable length of time, often three to four months. The plant itself will usually deteriorate before flowering actually ceases.

Buds: Are flatly folded and progressively develop as the main flowering stem continues to grow and initiates new flowering parts. The flowering bud closely resembles the shape of a lima bean but develops into a uniformly symmetrical flower.

Tepals: The upper side of the tepals is a dark red, 44A to 42A with the under side being 45B.

Reproductive organs: Flowers are very predominately male; female flowers, when they occur, are terminal.

*Stamens/anthers.*—Darker yellow than Krefeld Orange, with red pigmentation. They typically turn quite dark at maturity.

*Pollen.*—Dirty yellow, 13B.

*Styles/ovaries.*—None seen to date.

I claim:

1. A new and distinct cultivar of begonia characterized particularly as to uniqueness when compared to the parent cultivar Krefeld Orange by dark red tepals which quite frequently are six in number, and by its anthers which are a deeper yellow than the anthers of Krefeld Orange.

No references cited.

ROBERT E. BAGWILL, Primary Examiner